United States Patent
Mustafa et al.

[11] Patent Number: 5,932,557
[45] Date of Patent: Aug. 3, 1999

[54] ADENOSINE $A_1$ RECEPTOR ANTISENSE OLIGONUCLEOTIDE TREATMENT OF ALCOHOL AND MARIJUANA-INDUCED PSYCHOMOTOR IMPAIRMENTS

[76] Inventors: S. Jamal Mustafa, 419 Kempton Dr., Greenville, N.C. 27834; M. Saeed Dar, 115 Heritage St., Greenville, N.C. 27858

[21] Appl. No.: 08/909,868

[22] Filed: Aug. 12, 1997

[51] Int. Cl.$^6$ .......................... A61K 48/00; C07H 21/04; C12Q 1/68; C12N 15/85
[52] U.S. Cl. .................................. 514/44; 435/6; 435/91; 435/325; 435/354; 435/375; 536/23.1; 536/24.3; 536/24.31; 536/24.5
[58] Field of Search .......................... 435/6, 91.1, 172.3, 435/320.1, 354, 375; 536/23.1, 24.3, 24.31, 24.5; 514/44

[56] References Cited

U.S. PATENT DOCUMENTS 5,320,962  6/1994  Stiles et al. ........................... 435/252.3

OTHER PUBLICATIONS

Rojanasakul, Antisense Oligonucleotide Therapeutics: Drug Delivery and Targeting, Advanced Drug Delivery Reviews 18, 115–131 (1996).

Gewirtz, Facilitating Oligonucleotide Delivery: Helping Antisense Deliver on its Promise, PNAS 93, 3161–3163 (1996).

*Primary Examiner*—John L. LeGuyader
*Assistant Examiner*—Mark L. Shibuya
*Attorney, Agent, or Firm*—Jenkins & Wilson, P.A.

[57] ABSTRACT

Preclinical studies in mice and rats based on three microinfusions (12 hours apart) of specifically designed and synthesized adenosine $A_1$ receptor antisense oligonucleotide with the sequence: ($A_1$Antisense: 5'-GGCCGAGATGG AGGGCGGCAT-3' (SEQ ID NO: 1)) and as a control, a mismatched antisense nucleotide with a sequence: ($A_1$Sense: 5'-ATGCCGCCCTCCATCTCGGCC-3' (SEQ ID NO: 1)) established that the "functional knock out" of $A_1$ receptors protected the animals from the well known motor incoordination due to alcohol or $\Delta^9$-tetrahydrocarnabinol (THC: the major psychoactive component of marijuana intake). The motor coordination in animals was evaluated by the mouse/rat rotorod treadmill. The antisense was microinfused in mouse cerebellum and in the rat motor cortex whereas ethanol was always administered systemically. However, unlike ethanol, the $\Delta^9$-THC was microinfused into the mouse cerebellum following the cerebellar pretreatment with the antisense. In addition to protection of alcohol or the $\Delta^9$-THC-induced motor incoordination the above antisense molecule should block all functions expressed via adenosine $A_1$ receptor, such as hypnosis and general CNS intoxication, thereby, further expanding the clinical applications of this oligonucleotide. This antisense may also be useful in treating asthma and anginal chest pains.

9 Claims, 4 Drawing Sheets

ADENOSINE $A_1$ RECEPTOR ANTISENSE OLIGONUCLEOTIDE TREATMENT OF ALCOHOL AND MARIJUANA-INDUCED PSYCHOMOTOR IMPAIRMENTS

BACKGROUND OF THE INVENTION

1. Technical Field

The present invention relates generally to compositions including and methods utilizing antisense oligonucleotides, and more particularly to the use of an adenosine $A_1$ receptor antisense oligonucleotide in the prevention/treatment of alcohol and/or marijuana induced psycho-motor impairments.

2. Background Art

Alcohol and marijuana (*Cannabis sativa*) are among the oldest and most widely used drugs in the world. The major psychoactive ingredient of the marijuana plant is delta$^9$-tetrahydrocannabinol ($\Delta^9$-THC) (Razdan, 1986). One of the characteristic pharmacological effects produced by alcohol and $\Delta^9$-THC is motor impairment (MI), such as ataxia and a decrease in spontaneous motor activity (Hollister, 1986; Dewey, 1986). The impairment of motor functions by cannabinoid is well correlated with the presence of high density cannabinoid binding sites in the cerebellum and the basal ganglia (Herkanham et al., 1990; Mailleux and Vanderhaeghen, 1992). It has been suggested that the cannabinoid-induced motor impairments are due to cerebellar mediation (Herkanham et al., 1990).

Motor impairment in humans is one of the well known adverse consequences of alcohol drinking and marijuana smoking. Thus, marijuana and alcohol appear to produce, in a dose-related manner, a detrimental effect on the ability to drive an automobile. The consequences of use of both psychoactive drugs can be adverse not only for the drinker and smoker, respectively, but also for the safety of passengers in the drinker and smoker's automobile as well as for other non-smoking and non-drinking drivers. A striking deterioration of aircraft handling by pilots was demonstrated even 24 hours after smoking marijuana. Complex processes, including perception, attention, and information processing, which are involved in driving and flying, are impaired by doses equivalent to one or two cigarettes; the MI lasts for 4 to 8 hours, far beyond the time that the user perceives the subjective effects of the drug. A significant percent of marijuana users failed roadside sobriety test even 90 minutes after its smoking (Hollister, 1986). It is also well known that a high percentage of accident victims have ethanol in their blood. Furthermore, marijuana and alcohol are commonly used together. Ataxia and MI are the most conspicuous physical manifestation of alcohol consumption in animals and humans (Wallgren and Barry, 1970; Ritche, 1980). The MI produced by alcohol is additive to that induced by marijuana, resulting in rapid deterioration of driving performance (Dimijian, 1978; Reeve et al., 1985). These findings bear serious implications for driving, flying, operating rail/ship or performance of other complex tasks, even as long as a day after smoking marijuana and/or drinking alcohol. $\Delta^9$-THC and other cannabinoids produce variety of pharmacological effects which appear to be mediated by the recently characterized cannabinoid receptors (Herkanham et al., 1990) in both humans and laboratory animals. Some of these pharmacological properties are unique to $\Delta^9$-THC and psychoactive cannabinoids such as static ataxia in dogs and discriminative stimulus properties. The cannabinoids also possess many other properties such as analgesic, antiemetic, anticonvulsant and hypothermic which are shared by other drug groups. The recent identification and cloning of a specific cannabinoid receptor suggests that cannabinoids mimic endogenous compounds affecting neural signals for mood, memory, movement and pain. Cannabinoids have been reported to inhibit N-type calcium channels in neuroblastoma-glioma cells involving pertussis toxin-sensitive GTP-binding protein between cannabinoid receptors and calcium channels (Mackie and Hille, 1992). Some of the psychoactive effects of cannabinoids could be due to a calcium channel inhibition-induced decrease in excitability and neurotransmitter release (Mackie and Hille, 1992).

The pharmacological effects of adenosine (Dunwiddie and Worth, 1982; Crawley et al., 1981) bear similarity with some of the CNS effects of ethanol as well as $\Delta^9$-THC such as causing MI and being, anticonvulsant, hypothermic and anticiceptive. The modulation of MI due to alcohol by brain adenosine has been first reported by us (Dar et al., 1983) and later confirmed and extended by other investigators (Proctor and Dunwiddie, 1984) as well as by us (Clark and Dar, 1988, 1989a, b, c; 1991; Dar, 1986, 1988, 1989, 1990a, b; 1992; 1995, 1996, 1997; Dar et al., 1993, 1994; Meng and Dar, 1994, 1995, 1996; Anwer and Dar, 1995a, b). Results from these studies have shown that adenosine agonists and antagonists when administered systemically (Dar et al., 1983; Clark and Dar, 1988) or icv (Dar, 1989, 1990a, 1992), significantly accentuate and attenuate, respectively, acute ethanol-induced MI and inhibition of spontaneous motor activity (SMA) mainly via $A_1$ and less likely through $A_2$ subtype of adenosine receptors (Clark and Dar, 1988; Dar, 1990a). Overall, these data suggest a possible functional relationship between ethanol-induced MI and $A_1$ binding sites (Clark and Dar, 1988; Dar, 1990a). In addition, co-localization of adenosine $A_1$ and cannabinoid receptors on the axons and axonal terminals of the glutamatergic granule cells in the cerebellum has been demonstrated (Pacheco et al., 1993).

Although adenosine fulfills some of the classical criteria of a neurotransmitter, the impact of this is diminished by the realization that most tissues can release adenosine in response to metabolic demand. Adenosine may thus act as a "retaliatory" metabolite (Newby, 1984) because it inhibits cell function, reduces the release of excitatory neurotransmitters and induces local vasodilatation. Adenosine, however, has been considered to act as a neuromodulator (Williams, 1989), a homeostatic regulatory substance (Schmitt, 1984) and even a neurotransmitter (Phillis and Wu, 1981). Also, adenosine is well known to produce distinct phyiological and pharmacological actions (Phillis and Wu, 1981; Snyder, 1985; Dunwiddie, 1985; Ribeiro and Sebastiao, 1986). For example, adenosine and its analogs depress firing of central neurons (Phillis and Wu, 1981), inhibit release of various neurotransmitters in brain tissue and modulate ion channels (Dunwiddie, 1985). These important neuroactive actions of adenosine are mediated via well recognized, methyl xanthine-sensitive extracellular receptors probably by modulating second messenger systems such as adenylate cyclase (Phillis and Barraco, 1985), inositol phospholipid metabolism (Rubio et al., 1989), or calcium homeostasis in brain tissues via direct interaction with calcium channels (Ribeiro and Sebastiao, 1986). The behavioral effects of adenosine have generally been studied using stable analogs of adenosine (Proctor and Dunwiddie, 1984; Barraco, 1985; Phillis et al., 1986). Many of these behavioral effects can be mimicked by drugs which alter endogenous levels of brain adenosine such as adenosine deaminase inhibitors and adenosine uptake blockers (Phillis et al., 1986).

SUMMARY OF THE INVENTION

Currently, no drug is available to treat and/or prevent the marked motor incoordination and motor deficits that follow consumption of alcohol and/or smoking of marijuana. Both psychoactive drugs are well known in causing significant impairment of motor skills including automobile driving or operating machinery. The adverse and even fatal consequences of alcohol drinking and/or smoking marijuana are well known. Besides motor incoordination, these psychoactive drugs produce several other toxic manifestations such as mental confusion, sedation, changes in short-term memory, inability to concentrate. These toxic responses are experienced by virtually every user of these agents.

The involvement of adenosine $A_1$ receptor in the expression of at least motor incoordination due to alcohol use has been well established first reported by Dar et al as early as 1983. The possible role of adenosine $A_1$ receptor in the motor impairment produced due to $\Delta^9$-THC has also been observed in our laboratory recently. Using the molecular approach, adenosine $A_1$ receptor antisense oligonucleotide was designed and synthesized in order to functionally "knock out" the $A_1$ receptor, thereby, virtually preventing the motor incoordination due to alcohol and/or $\Delta^9$-tetrahydrocannabinol ($\Delta^9$-THC). Therefore, adenosine $A_1$ antisense oligonucleotide with the following sequence: ($A_1$ Antisense: 5'-GGCCGAGATGGAGGGCGGCAT-3') (SEQ ID NO: 1)) and as a control, a mismatched antisense nucleotide ($A_1$ Sense: 5'-ATGCCGCCCTCCATCTCGGCC-3')(SEQ ID NO: 2)); provides a novel approach to the clinical management of alcohol and/or marijuana-induced motor deficits and may reduce the adverse consequences of alcohol/marijuana use on automobile driving as well as other motor tasks. The $A_1$ antisense can also treat motor disabilities and sedation caused by other classes of drugs such as narcotic analgesics (morphine, heroin), gabamimetic drugs and benzodiazepines such as Valium, Librium.

The intracerebellar (ICB) $\Delta^9$-THC-induced MI was demonstrated by establishing a dose-response relationship using rotorod treadmill procedure. Intra cerebellar microinfision of 15, 20, 25, and 30 $\mu g$ of $\Delta^9$-THC produced nearly a dose-related MI. The presence of $A_1$ but not $A_2$ receptor subtype in the cerebellum has been reported which may circumstantially suggest the importance of the role of $A_1$ subtype in MI. Direct support for the role of adenosine $A_1$ receptors in $\Delta^9$-THC-induced MI is obtained by the rotorod studies in which animals were pretreated with adenosine $A_1$ antisense and sense oligonucleotide. The studies based on an adenosine $A_1$ antisense oligonucleotide provided the direct evidence that the adenosine $A_1$ subtype is mediating the adenosine modulation of $\Delta^9$-THC-induced MI. The mouse adenosine $A_1$ receptor has so far not been cloned. However, the cloning of the adenosine $A_1$ receptors of the rat, rabbit and human has been reported. A possibility of limited mutation with little differences in the sequence of adenosine $A_1$ receptors in the mouse and the rat was considered after comparison of sequences of $A_1$ clones of different animal species. Consequently, we expected to observe significant alteration in the motor response after treatment with an antisense oligonucleotide in mice in the event of $A_1$ mediation, even though as stated above the latter synthesis was based on information of cloned rat $A_1$ receptor. Indeed, marked attenuation of $\Delta^9$-THC-induced MI as well as an inhibition of accentuation by adenosine agonist of $\Delta^9$-THC-induced MI has been observed. The anticipated functional "knockout" of the adenosine $A_1$ receptors' gene expression in the micro infusion site in the cerebellum due to antisense pretreatment most likely may have occurred. The antisense oligonucleotide caused a selective attenuation of the $\Delta^9$-THC-induced MI as well as an attenuation of adenosine $A_1$-selective agonist-induced accentuation of MI due to $\Delta^9$-THC, therefore, it will be logical to assume a decrease in the $A_1$ receptor expression. The adenosine $A_1$ antisense oligonucleotide after ICB pretreatment functionally "knocked out" completely $\Delta^9$-THC-induced MI and markedly antagonized adenosine $A_1$-selective agonist-induced accentuation of $\Delta^9$-THC's MI.

In view of the frequent simultaneous use of marijuana and alcohol, possible motor behavioral interactions between $\Delta^9$-THC and alcohol was established. The ICB effect of $\Delta^9$-THC on ethanol (i.p.)-induced MI indeed has been observed by us to result in aggravated MI. This is in agreement with the well known additive and detrimental effects of simultaneous use of both psychoactive drugs on motor functions and its profound adverse effects on automobile driving (Reeve et al., 1985). The specificity of motor behavioral interactions between $\Delta^9$-THC and alcohol can be judged from the observations based on which ethanol-induced ataxia was markedly potentiated by sub-ataxic ICB doses of $\Delta^9$-THC which were far below the minimal ataxic dose (15 $\mu g$) of $\Delta^9$-THC.

BRIEF DESCRIPTION OF THE DRAWINGS

FIG. 1 also shows significant potentiation of ethanol's MI by ICB adenosine agonist, CHA (●_●), which was also markedly antagonized by adenosine $A_1$ antisense (Δ_Δ). There was no effect of pretreatment with sense oligonucleotide on ethanol-induced MI as well as on CHA's potentiating effect of ethanol-induced MI (FIG. 1;x_x; and ■_■)

The effect of adenosine $A_1$ antisense oligonucleotide and the sense (2 $\mu$/100 nL) administered as an intracerebellar (ICB) microinfusion 3 times, once every 12 h, on ethanol ((ET) 2 g/kg,i.p.)-induced and CHA+ET-induced motor impairment. Each point represents the mean±S.E. of at least 10 mice. (o) ACSF 100 nL+ET; (Δ) antisense (pretreatments)+CHA 4 ng/100 nL+ET; (▲) antisense (pretreatments)+ACSF 100 nL+ET: (■) CHA 4 ng/100 nL+ET; (●) CHA 4 ng/100 nL+saline; (□) sense (pretreatments)+CHA 4 ng/100 nL+ET; (x) sense (pretreatments)+ACSF 100 nL+ET.

Figure 1:
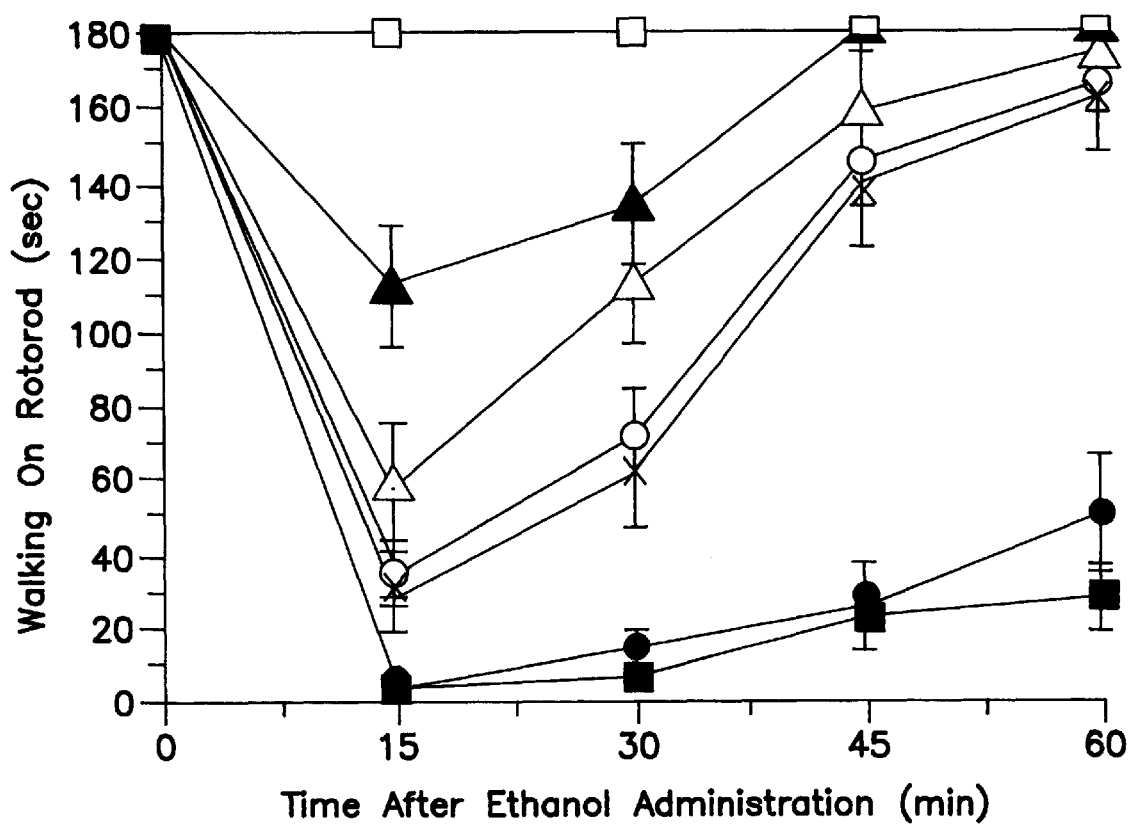
FIG. 1 shows that the test dose (2 g/kg,i.p.) of ethanol produces significant motor incoordination (MI), the peak effect observed within 15 min, and the animals almost regained their normal motor coordination by 60 min post-ethanol (O_O). The pretreatment with adenosine $A_1$ antisense markedly attenuated ethanol-induced MI (▲_▲).
Figure 2:
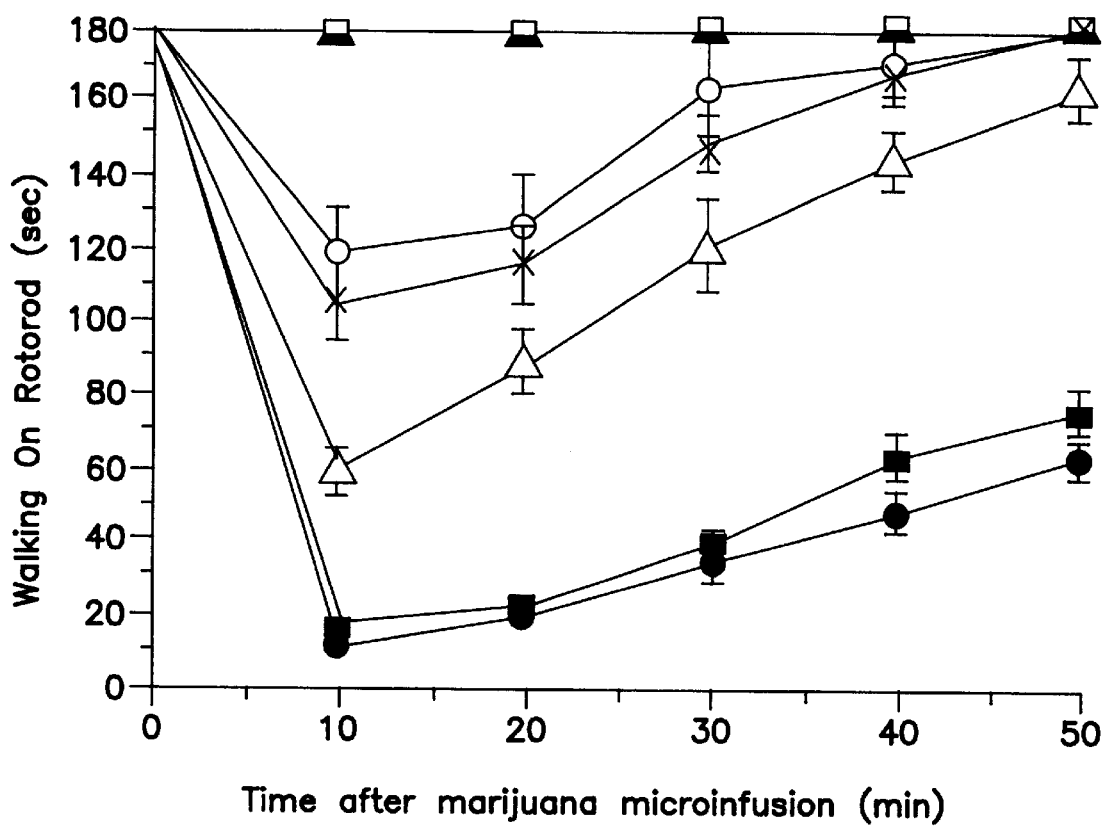

FIG. 2 shows a similar attenuating effect of adenosine $A_1$ antisense on MI produced by ICB micro infusion of $\Delta^9$-THC (O_O). Similarly, ICB microinfusion of CHA, markedly potentiated $\Delta^9$-THC-induced MI (●_●), which was markedly antagonized by pretreatment with adenosine $A_1$ antisense oligonucleotide (Δ_Δ). There was no effect of pretreatment with sense oligonucleotide on $\Delta^9$-THC-induced MI (x_x) as well as on the potentiating effect of ICBI microinfusion of CHA on $\Delta^9$-THC-induced MI (■_■). No effect on normal motor coordination was observed by CHA (□_□). The effect of adenosine $A_1$ antisense oligonucleotide and the sense (2 $\mu g$/100 nL) administered as an intracerebellar (ICB) microinfusion 3 times, once every 12 h, on marijuana (($\Delta^9$-THC); 15 $\mu g$/1 nL also ICB)-induced and CHA (ICB)+$\Delta^9$-THC(ICB)-induced motor impairment. Each point represents the mean±S.E. of at least 10 mice (o)

ACSF 100 nL+$\Delta^9$-THC; ($\Delta$) antisense (pretreatments)+CHA 4 ng/100 nL; (▲) CHA 4 ng/100 nL+$\Delta^9$-THC; (●) CHA 4 ng/100 nL+saline; (□) sense (pretreatments)+CHA 4 ng/100 nL+$\Delta^9$-THC; (x) sense+$\Delta^9$-THC.

Figure 3:
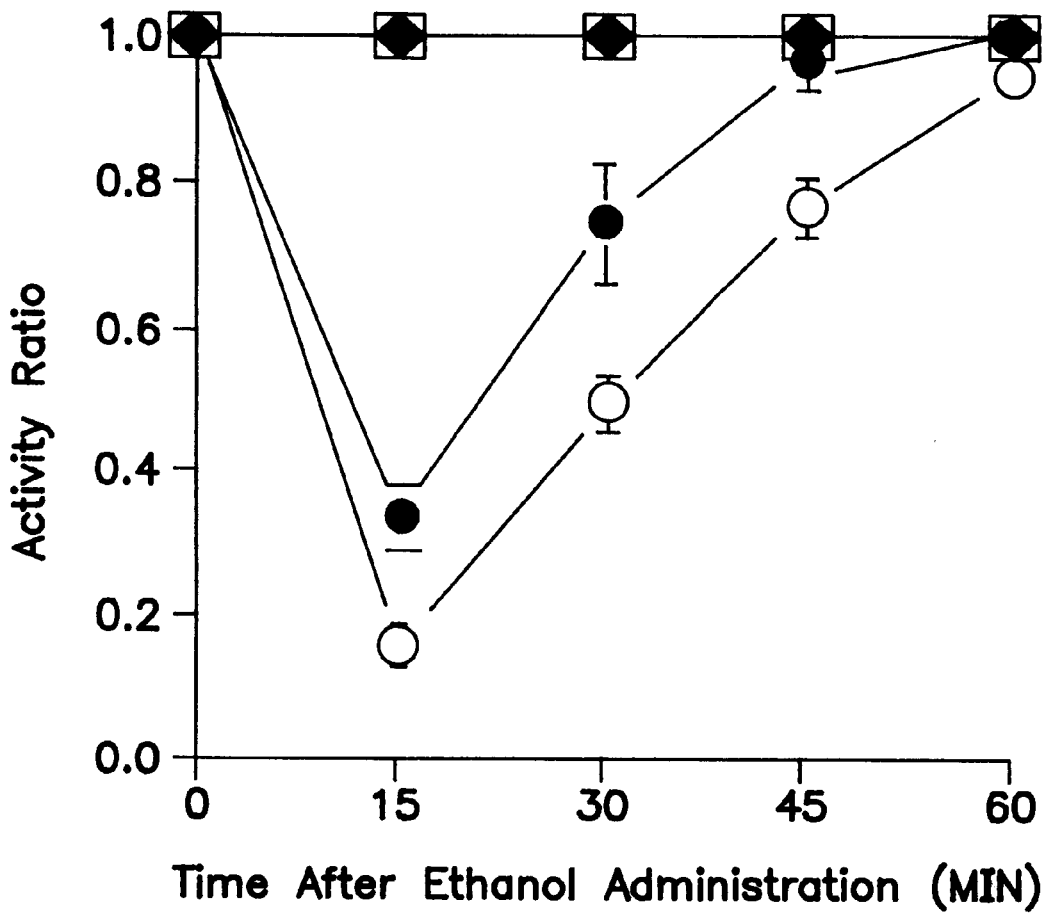
Figure 4:
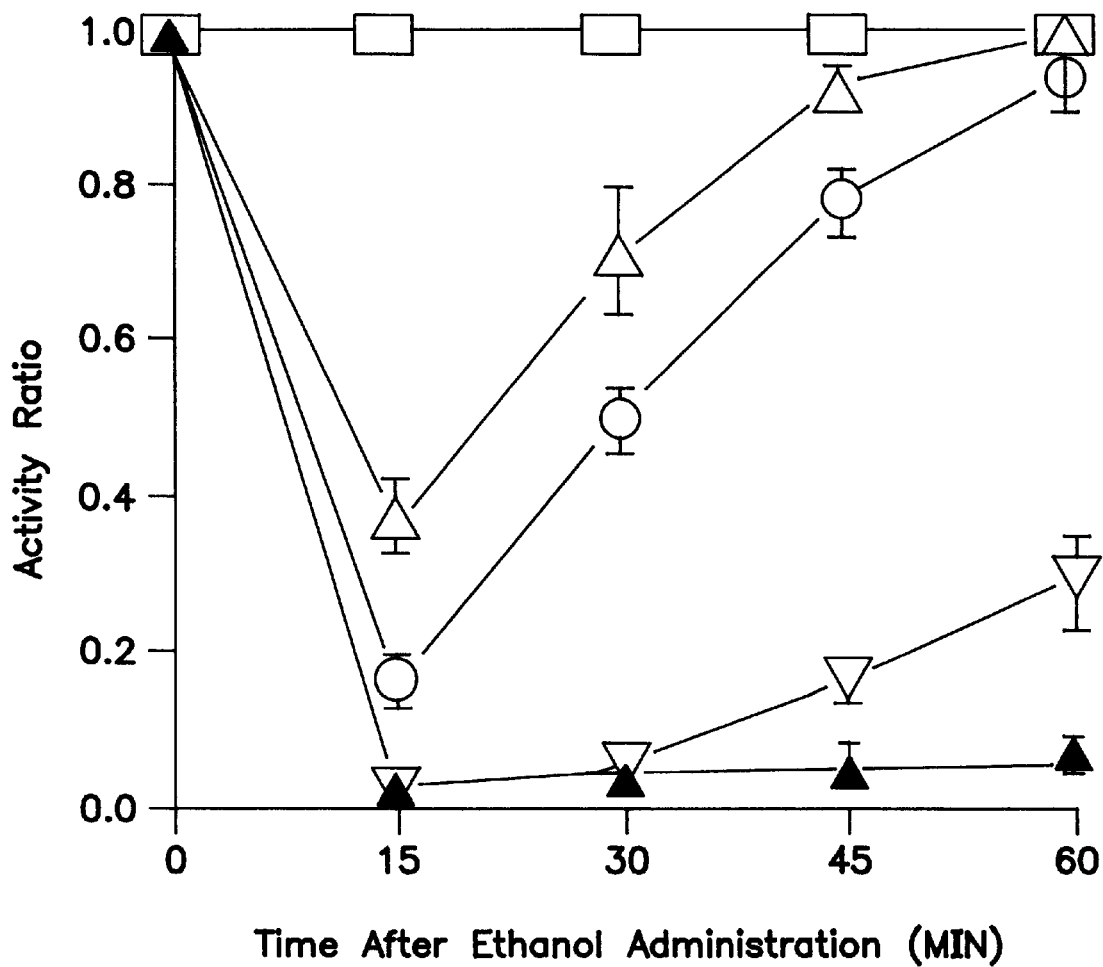

Similar results were observed (FIGS. 3 & 4) in the rat confirming the above observations that adenosine $A_1$ receptor antisense was eective in blocking the motor impairment induced by alcohol. The microinfusion dose of the antisense and the experimental details were the same as in the above studies. The site of the microinfusion of the antisense in the case of rat studies was, however, the motor cortex which is also another important brain area involved in motor control. FIG. 3 shows the effect of pretreatments of the motor cortex with adenosine $A_1$ receptor antisense and sense oligonucleotide (2 μg/200 nL) microinfused 3 times, once every 12 h, on ethanol ((ET): 1.5 g/kg,i.p.)-induced motor impairment. Each point represents the mean±S.E. of at least 5 rats. (○) ACSIF 200 nL+ET; (●) antisense (pretreatments)+ACSF 200 nL+ET; (□) antisense (pretreatments)+ACSF 200 nL+saline; (♦) sense (pretreatments)+ACSF 200 nL+saline. FIG. 4 shows the effect of adenosine $A_1$ receptor antisense and sense oligonucleotide (2 μg/200 nL) microinfused 3 times, once every 12 h, pretreatment of the motor cortex on the ability of CHA (intramotor cortex) to accentuate ethanol (ET; 1.5 g/kg, i.p.)-induced motor impairment. Each point represents the mean±S.E. of at least 5 rats. (○) ACSF 200 nL+ET; (▲) CHA 0.069 nmol/200 nL+ET; ($\Delta$) antisense (pretreatmerits)+CHA 0.069 nmol/200 nL+ET; (▽) sense (pretreatments)+CHA 0.069 nmol/200 nL+ET; (□) antisense (pretreatments)+ACSF 200 nL+saline

DETAILED DESCRIPTION OF THE INVENTION

The new knowledge about the involvement of an adenosinergic pathway in marijuana and/or alcohol-induced deficit in the performance of the motor tasks and the identification of the $A_1$ receptor mediating this effect in the brain resulted in the designing and synthesis of adenosine $A_1$ antisense oligonucleotide. An effective adenosine $A_1$ antisense oligonucleotide which was synthesized had the following sequence: 5'-GGCCGAGATGGAGGGCGGCAT-3' (SEQ ID NO: 1).

As a control, a mismatched phosphorothioate antisense nucleotide was also synthesized which had the following sequence: 5'-ATGCCGCCCTCCATCTCGGCC-3' (SEQ ID NO: 2)).

By functionally "knocking out" the $A_1$ receptors the antisense nucleotide protected the mice and rats from the motor deficit producing effect of the $\Delta^9$THC. $\Delta^9$-THC is the most potent psychoactive alkaloid of the marijuana plant. The motor deficit was evaluated by a laboratory model of mouse/rat rotatory treadmill. The results show that the above antisense can be used for the clinical management of marijuana and/or alcohol-induced motor deficits. The adenosine $A_1$ antisense oligonucleotide ($A_1$ Antisense: 5'-GGCCGAGATGGAGGGCGGCAT-3' (SEQ ID NO: 1)) and as a control, a mismatched (sense) antisense nucleotide ($A_1$ Sense: 5'-ATGCCGCCCTCCATCTCGGCC-3' (SEQ ID NO: 1)) used in the studies supporting this patent application was designed and synthesized based on rat cloned $A_1$ receptor. The rat and the human adenosine $A_1$ receptor are almost identical. There is 88% cDNA sequence homology; 97% amino acid sequence homology and $A_1$ receptor in both species have the same number (326) of amino acids and therefore should serve same biological functions. As a further elaboration of this important point, an adenosine $A_1$ antisense oligo which successfully "knocks out" adenosine A receptor should produce almost identical biological response. Consequently, all biological responses which are expressed through the participation of adenosine $A_1$ receptors regardless of species are likely to be influenced by $A_1$ antisense. This is the basis of proposed clinical applications of $A_1$ antisense oligonucleotide. Having regard to the foregoing disclosure the following is claimed as inventive and patentable embodiments thereof:

This adenosine $A_1$ antisense ($A_1$ Antisense: 5'-GGCCGAGATGGAGGGCGGCAT-3' (SEQ ID NO: 1)) and as a control, a mismatched antisense nucleotide ($A_1$ Sense: 5'-ATGCCGCCCTCCATCTCGGCC-3' (SEQ ID NO: 2)) can be used for the treatment of asthma and other inflammatory diseases where $A_1$ adenosine receptor has been shown to be involved. $A_1$ receptor in lung causes bronchospasm and turning off this $A_1$ adenosine receptor gene by the use of this antisense can cure asthma.

This adneosine ($A_1$ Antisense: 5'-GGCCGAGAT GGAGGGCGGCAT-3' (SEQ ID NO: 1)) and as a control, a mismatched antisense nucleotide ($A_1$ Sense: 5'-ATGCCGCCCTCCATCTCGGCC-3' (SEQ ID NO: 2)) can also be used to block the $A_1$ adenosine receptor in coronary artery because $A_1$ receptor causes anginal chest pains. Similarly, this adenosine ($A_1$ Antisense: 5'-GGCCGAGATGGAGGGCGGCAT-3' (SEQ ID NO: 1)) and as a control, a mismatched antisense nucleotide ($A_1$ Sense 5'-ATGCCGCCCTCCATCTCGGCC-3' (SEQ ID NO: 2)) can also be employed to block the $A_1$ receptor in brain circulation for preventing trans-ischemic attacks.

II. EXAMPLES

I. Intracerebellar (ICB) drug microinfusion (Example-1)

After surgical implantation with permanent indwelling cannulas into the cerebellar cortex, the mice were housed individually and given free access to commercial pellet food and tap water. To minimize possible infection, aseptic surgical techniques were used and the animals received (s.c.) 300 units of Durapen® (combination of benzathine and procaine penicillin G suspension) and an injection of analgesic (ketorolac; 2 mg/kg, i.p.) just after surgery and the analgesic injection repeated once after 4 hours.

(a) Surgery: (Example-2) Mice, under chloral hydrate (450 mg/kg, i.p) anesthesia, were stereotaxically implanted with permanent indwelling stainless-steel guide cannulas directed for microinfusion of a drug into the cerebellum with the skull surface in the horizontal plane (flat skull) according to coordinates of Slotnik and Leonard (1970). The coordinates for the cerebellar cannulation will be: AP, −6.4 (bregma); ML, +0.8; DV, −1.0, from skull surface. The other details were same as reported previously (Dar, 1990a, b; 1992; 1995).

b. Drugs: (Example-3) The drug solutions were prepared just prior to their microinfusion. The vehicle used for making solution of adenosine $A_1$ antisense and the sense was artificial cerebrospinal fluid (ACSF). The ICB microinfusion volume of antisense in mice was kept constant at 100 nL and given over 2 min period during which the animals were allowed to move freely in their home cages. At the time of microinfusion, the injector cannulas were connected to 100 μl Hamilton syringes by PE-10 (Clay Adams) polyethylene tubing and the drug solution will be delivered using Harvard Model 22 Pump (Harvard Apparatus, Mass.). Because 100% DMSO was used to reconstitute $\Delta^9$-THC, it was critical to rule out any MI effect due to ICB microinfusion of 1 μl of 100% DMSO. Since no change in the normal motor coordination was observed after ICB microinfusion of up to 5 μl of 100% DMSO, ACSF instead of DMSO, will be used in the control experimental groups in the proposed work. A test dose of 2 g/kg, i.p. of ethanol (10% w/v in saline) was used in the study.

c. Histology: (Example-4) Immediately following a behavioral experiment, 100 nL of India Ink was microinfused into each mouse through the same guide cannula, the mouse was then sacrificed and the brain removed. The brains were sectioned to confirm the drug microinfusion site. Only those mice in which the histological confirmation was made were included in the calculation of data.

II. Motor coordination test: (Example-5) The degree of motor impairment (MI) was determined using a standard rotorod treadmill (UGO Basile, Verese Italy) which was calibrated for a fixed speed of 20 rpm (Dar et al., 1983; Dar, 1990a, b,; 1992,1995,1996). Animals were allowed to acclimatize to the treadmill by placing them on it 2–3 times few min prior to the actual experiment. The screening test now used in our laboratory requires each animal to remain on the rotorod for 180 s. The successfully screened animals received the pretreatment (ACSF/adenosine agonist [CHA] or anti-sense/sense oligonucleotide), followed 2 min later by the ICB micro infusion of $\Delta^9$-THC (15 µg) or a test dose of ethanol (2.0 g/kg; i.p.). The index of motor coordination will always be evaluated every 10 min for 50 and 60 min starting from the moment of $\Delta^9$-THC microinfusion or ethanol injection, respectively.

The pre-set criterion of 180 s stay on the rotorod will be the basis to evaluate the effect of $\Delta_1$ antisense pretreatment on ethanol or $\Delta^9$-THC-induced MI. The effect of $A_1$ antisense pretreatment on $\Delta^9$-THC-induced MI could cause the animals to stay on the rotorod for less than, greater than or nearly the same period relative to the period they stayed on the rotorod when treated with ACSF+$\Delta^9$-THC or ethanol. The animals in each rotorod experiment acted as their own control and were not used again after the conclusion of each experiment.

After the successful prescreening of the mice, one group of five mice was given 2 µg/100 nL of the anti-sense oligonucleotide through ICB microinfusion. The microinfusion of antisense was repeated every 12 hr twice i.e. total of three microinfusions of 2 µg each were administered. Twelve hours following the last microinfusion, the animals were prescreened on rotorod as explained above. After successful prescreening, the animals that were pretreated with the antisense oligonucleotide, were given 100 nL ACSF, followed within 2–5 min, the test dose (2 g/kg, i.p.) of ethanol. The motor coordinatioe was evaluated every 15 min after ethanol-injection for up to 60 min post-ethanol. Similarly, another group of prescreened mice was pretreated with antisense exactly in the same manner as stated above. Twelve hours after the last antisense microinfusion, the motor coordination was evaluated following ICB microinfusion of adenosine agonist, CHA (4 ng/100 nL) and test dose of ethanol. Experiments in which pretreatment with the same dose of sense oligonucleotide were also carried out in groups of five mice each, according to same protocol as with the antisense. This was needed to evaluate the effect of test dose of ethanol and of CHA+ethanol on motor coordination. Separate motor coordination experiments were conducted to evaluate the effect of test dose of ethanol, the effect of intracerebellar microinfusion of CHA with/without ethanol on motor coordination. Similar studies were repeated with $\Delta^9$-THC instead of ethanol in which the test dose (15 µg) of $\Delta^9$-THC was given by ICB microinfusion and not by i.p. injection to groups of mice pretreated with anti-sense and sense oligonucleotide.

III. Specifications: (Example 6) The $A_1$ adenosine antisense oligonucleotide bearing the following structure: ($A_1$ Antisense: 5'-GGCCGAGATGGAGGGCGGCAT-3' (SEQ ID NO: 1)) and as a control a mismatched antisense nucleotide ($A_1$ Sense: 5'-ATGCCGCCCTCCATCTCGGCC-3' (SEQ ID NO: 2)); should be administered by dissolving either in normal physiological saline, physiological buffers, or be used as capsule mixed with non-toxic carrier as a diluent for oral route administrations. It can also be administered parenterally by dissolving it either in a sterile normal physiological saline or sterile physiological buffers.

We claim:

1. An adenosine $A_1$ receptor antisense oligonucleotide having the nucleotide sequence 5'-GGCCGAGATGGAGGGCGGCAT-3' (SEQ ID NO: 1).

2. An adenosine $A_1$ receptor sense oligonucleotide having the nucleotide sequence 5'-ATGCCGCCCTCCATCTCGGCC-3' (SEQ ID NO: 2).

3. A pharmaceutical composition comprising an adenosine $A_1$ receptor-attenuating amount of the adenosine $A_1$ receptor antisense oligonucleotide of claim 1, and a pharmaceutically acceptable diluent.

4. The composition of claim 3, wherein the adenosine $A_1$ receptor-attenuating amount of the adenosine $A_1$ receptor antisense oligonucleotide ranges from 0.01 mg to 1000 mg.

5. The composition of claim 3, wherein the pharmaceutical composition is adapted for administration in a form selected from the group consisting of oral form, aerosol form, parenterally injectable form, infusible form, and combinations thereof.

6. A method of attenuating adenosine $A_1$ receptor-mediated motor incoordination in a mammal, the method comprising the step of administering to the mammal an adenosine $A_1$ receptor-attenuating amount of an adenosine $A_1$ receptor antisense oligonucleotide having the nucleotide sequence 5'-GGCCGAGATGGAGGGCGGCAT-3' (SEQ ID NO: 1), whereby attenuation of adenosine $A_1$ receptor-mediated motor incoordination is accomplished.

7. The method of claim 6, wherein the adenosine $A_1$ receptor-attenuating amount of the adenosine $A_1$ receptor antisense oligonucleotide ranges from 0.01 mg to 1000 mg.

8. The method of claim 6, wherein the oligonucleotide is in a physiologically compatible form and wherein the step of administering is accomplished in a manner of administration selected from the group consisting of oral administration, aerosol administration, parenteral administration, infusion administration, and combinations thereof.

9. The method of claim 6, wherein the adenosine $A_1$ receptor-mediated motor incoordination is selected from the group consisting of alcohol-induced motor incoordination, marijuana-induced motor incoordination, and combinations thereof.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:1:

GGCCGAGATG GAGGGCGGCA T          21

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:2:

ATGCCGCCCT CCATCTCGGC C          21